United States Patent
Engstad et al.

(10) Patent No.: US 10,646,506 B2
(45) Date of Patent: *May 12, 2020

(54) GLUCANS

(71) Applicant: BIOTEC PHARMACON ASA, Tromsø (NO)

(72) Inventors: Rolf Engstad, Tromsø (NO); Thor Nøkland, Tromsø (NO)

(73) Assignee: Biotec Pharmacon Asa, Tromsø (NO)

( * ) Notice: Subject to any disclaimer, the term of this patent is extended or adjusted under 35 U.S.C. 154(b) by 332 days.

This patent is subject to a terminal disclaimer.

(21) Appl. No.: 15/350,230

(22) Filed: Nov. 14, 2016

(65) Prior Publication Data

US 2017/0056433 A1    Mar. 2, 2017

Related U.S. Application Data

(63) Continuation of application No. 13/989,580, filed as application No. PCT/GB2011/052357 on Nov. 29, 2011, now Pat. No. 9,623,043.

(30) Foreign Application Priority Data

Nov. 29, 2010    (GB) .................................. 1020190.3

(51) Int. Cl.
| | | |
|---|---|---|
| A61K 31/716 | (2006.01) | |
| A61K 31/00 | (2006.01) | |
| C08B 37/00 | (2006.01) | |
| A61K 9/06 | (2006.01) | |
| A61K 9/70 | (2006.01) | |

(52) U.S. Cl.
CPC .............. *A61K 31/716* (2013.01); *A61K 9/06* (2013.01); *A61K 9/70* (2013.01); *A61K 31/00* (2013.01); *C08B 37/0024* (2013.01)

(58) Field of Classification Search
None
See application file for complete search history.

(56) References Cited

U.S. PATENT DOCUMENTS

| | | |
|---|---|---|
| 5,082,936 A | 1/1992 | Jamas et al. |
| 5,158,772 A | 10/1992 | Davis |
| 5,322,841 A | 6/1994 | Jamas et al. |
| 6,242,594 B1 | 6/2001 | Kelly |
| 6,875,754 B1 | 4/2005 | Griesbach et al. |
| 2003/0185863 A1 | 10/2003 | Bengs et al. |
| 2004/0023923 A1 | 2/2004 | Morgan |
| 2005/0255565 A1 | 11/2005 | Engstad |
| 2009/0004201 A1 | 1/2009 | Engstad |
| 2010/0322923 A1 | 12/2010 | Seljelid et al. |

FOREIGN PATENT DOCUMENTS

| | | |
|---|---|---|
| WO | 9530022 A1 | 11/1995 |
| WO | 9628476 A1 | 9/1996 |
| WO | 9921531 A1 | 5/1999 |
| WO | 02058711 A1 | 8/2002 |
| WO | 2004039378 A1 | 5/2004 |
| WO | 2006123173 A1 | 11/2006 |
| WO | 2007062995 A1 | 6/2007 |
| WO | 2009043319 A1 | 4/2009 |
| WO | 2009063221 A2 | 5/2009 |
| WO | 2011011617 A1 | 1/2011 |

OTHER PUBLICATIONS

Pu Qinglin, "Research on Interaction of Yeast Glucan With Other Macromolecular Substances", China Excellent Doctoral and Master's Theses (Master) Engineering Science and Technology vol. I, Issue 2, Feb. 15, 2007, with English-language translation (94 pages with translation).

Matsuda, Kazuo (Jul. 1, 1999) "Separation and Purification Method of Polysaccharides" Seibutukagaku Jikkenhou, vol. 20, pp. 23-28, Center for Academic Publications Japan, Co. Ltd., Jul. 1, 1999, with English-language translation.

Sletmoen, Marit, et al., "Review Higher Order Structure of (1,3)-β-D-Glucans and Its Influence on Their Biological Activities and Complexation Abilities," Biopolymers, vol. 89, No. 4, pp. 310-321 (2008).

Steiner, E., et al., "Rheological properties of solutions of a colloid-disperse homoglucan from Schizophyllum commune," Progress in Colloid & Polymer Science, vol. 77, pp. 217-220 (1988).

Xu, Jingyuan, et al., "Micro-heterogeneity and micro-rheological properties of high-viscosity oat β-glucan solutions," Food Chemistry, vol. 103, pp. 1192-1198 (2007).

*Primary Examiner* — Layla D Berry
*Assistant Examiner* — Bahar Craigo
(74) *Attorney, Agent, or Firm* — Rothwell, Figg, Ernst & Manbeck, P.C.

(57) ABSTRACT

The present invention relates to a glucan having a weight average molar mass of 15,000 to 50,000 g/mol on a single chain basis and a weight average molar mass in aqueous solution on an aggregate basis of 4 to $20 \times 10^5$ g/mol and existing in gel form in aqueous solution at a concentration ≥1% at 25° C. and neutral pH and having a melting temperature (gel to sol) of 30 to 44° C. when the glucan is dissolved in water at a concentration of 2%, methods for the production thereof, medical uses thereof, physical supports having the glucan applied thereto or impregnated thereon and in vitro methods of proliferation of skin cells which comprise contacting a population of skin cells with the glucan.

17 Claims, 7 Drawing Sheets

GLUCANS

CROSS-REFERENCE TO RELATED APPLICATIONS

Figure 1:
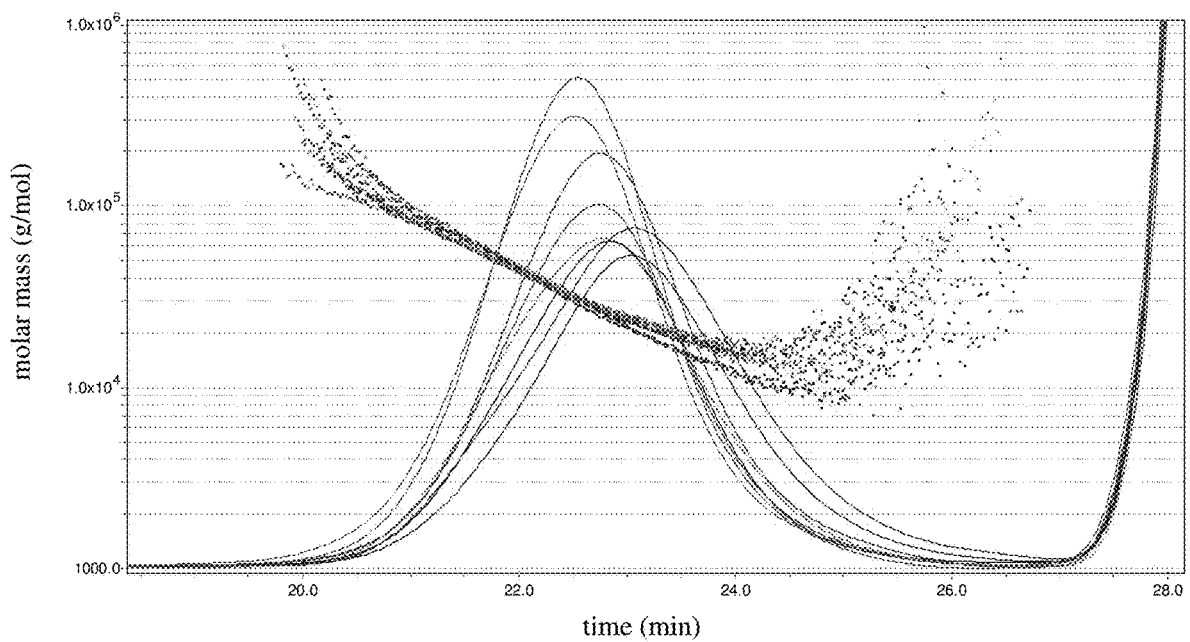

This application is continuation of U.S. patent application Ser. No. 13/989,580 filed 9 Aug. 2013, which in turn is a filing under 35 USC 371 of International Application No. PCT/GB2011/052357, filed 29 Nov. 2011, which claims priority to GB Application No. 1020190.3, filed 29 Nov. 2010. Each application is incorporated herein by reference.

The present invention relates to a new glucan product, to processes for its manufacture and to uses thereof as a pharmaceutical, incorporated in a medical device, as a nutraceutical, cosmetic product or the like.

Glucans are a heterogeneous group of glucose polymers found in amongst others the cell walls of plants, bacteria, fungi and protozoa. Glucans have a backbone chain and in some cases side chains which, depending of the origin of the glucan, comprise β(1,3), β(1,4) and/or β(1,6)-linked glucosyl units. Depending upon the source and method of isolation, beta-glucans have various degrees of branching and type of linkage in the backbone and side chains. The frequency and type of linkage in the side chains is highly relevant to the molecule's biological activity. Glucans also differ highly in their molecular weight as well as in their tendency for chain aggregation which both are essential features for the efficacy profile of these molecules. Most beta-glucans of fungal and yeast origin are in their native state insoluble in water, but can be made soluble either by acid hydrolysis or by derivatization introducing foreign groups like -phosphate, -sulphate, -amine, -carboxymethyl and so forth to the molecule.

In Europe, Asia and USA, beta-glucans especially from Bakers' yeast have long been employed as feed additives for animals, in cosmetics, as dietary supplement for humans, as immunomodulators e.g. in treatment of wounds, and as an active ingredient in skin cream formulations. Glucans have been employed in the treatment of cancer as shown in WO02/058711. Beta-glucans are, in this context, regarded as immunostimulants increasing the activity of white blood cells partly by inducing well regulated and site restricted inflammatory reactions localised to the cancer. Their use in the treatment of inflammatory bowel disease has also been described in WO 2009/063221. Further applications of glucans within wound treatment are described in EP 815144 and in U.S. Pat. No. 6,875,754 as well as for the treatment of asthma and allergy as described in U.S. Ser. No. 12/528, 215.

Cereal glucans comprise generally unbranched chains of β(1,3) and a significant share of β(1,4) linkages while yeast glucans are made up of predominantly β(1,3) linked glucosyl residues with β(1,6) linkages acting as branch points for side chains which may comprise both β(1,3) and β(1,6) linked glucosyl residues. Other molecules classed as glucans include curdlan, a basically linear molecule made up of β(1,3) linked glucosyl residues without branches. Lentinan is a glucan with a β(1,3) linked backbone but incorporating single β(1,6) linked glucosyl residues attached essentially regularly to the backbone giving a haircomb structure of this molecule. The single β(1,6) linked glucosyl residues attached to the backbone equivalent to a β(1,3,6) linkage point but no further molecules are attached to this linkage point and thus glucans like lentinan do not have side chains. Other examples of this group of glucans are scleroglucan, laminarin and schizophyllan.

Variations in branching and the length and structure of the side chains lead to contrasting secondary and tertiary structures and thus biological activities. The higher order structures of glucans vary considerably and molecular weight, solubility and particle size will all influence activity in a generally unpredictable manner. Some products are extremely potent inducers of inflammatory cytokines in target cells, whereas others have the opposite effect, completely inhibiting cytokine release. Typical for many insoluble beta-glucan products is the induction of a whole range of inflammatory responses, where e.g. injection of insoluble beta-glucan formulations has been associated with granuloma formation, arthritis induction and increased susceptibility against gram negative sepsis. On the other side, soluble beta-glucans are not reported to be encumbered with such negative side effects, but their efficacy as immunostimulants have been known to vary substantially.

It has been shown (WO 95/30022), for example, that a glucan product derived from yeast which has been modified by glucanase treatment to selectively remove (1,6) linked side chains is more potent in stimulating the immune system of fish than a product with intact (1,6) linked side chains.

Glucans have great potential as therapeutic agents and adjuvants but the vast range of structural variability, problems of analysis with such large and complex molecules and the lack of understanding about mechanism of action and receptors for these molecules, means that there is still a great need for an improved glucan product and for controllable and repeatable processes for manufacture of homogeneous products. The present invention addresses these problems. The present invention potentiates glucan efficacy by manipulating the primary and secondary molecular structure of a glucan to establish a pharmaceutically beneficial tertiary structure in the final product.

Beta-glucans are known to be so-called Pathogen Associated Molecular Patterns as they are found at the surface of a number of pathogenic (micro)organisms, especially fungi. Higher organisms have thus evolved mechanisms for recognizing these types of structures in order to find and destroy intruders belonging to this class of organism. In mammals the so called innate immune cells express specific receptors recognizing beta-glucans, and one of the most prominent receptors is called Dectin-1, but other receptors are also involved in the recognition or signal transduction induced by beta-glucans amongst these are CD11b/CD18 (CR3), and toll receptors 2 and 4 (TLR2 and TLR4). Of the cells involved in recognizing beta-glucans are the typical phagocytes of the innate immune system, i.e. monocyte, macrophages, dendritic cells, and granulocytes, but also Natural Killer cells as well as a number of endothelial cells and other more tissue specific cells have the ability to express beta-glucan receptors.

The crucial step in inducing a biological response in the target cells is the initial binding to the receptor and furthermore, it seems, the ability of the beta-glucan formulation to cross-link a sufficient number of receptors in order to induce an adequate signal-transduction into the cell. The present invention describes a product and a method for making a product that has the ability to cross-bind receptors inducing a specific type of biological activity. This is in contrast to insoluble products that could induce a massive response by cross-binding a large number of receptors and secondly be phagocytosed, which due to the nature of the insoluble (or "crystalline like") glucan leads to lysosomal rupture within the cell inducing NLRP inflammasome activation. Insoluble beta-glucans may also induce ROS (reactive oxygen species) that also would trigger inflammasome activation leading to an unfavorable inflammatory reaction. The current invention describes beta-glucans products that are able to induce a significant inflammatory response that would activate several immune mechanisms, but without triggering inflammasome activation that is typical for a number of (aggregated insoluble) beta-glucan products.

The present invention potentiates glucan efficacy by establishing a pharmaceutically beneficial supramolecular structure in the final product.

The importance of higher order structure amongst β-glucans and the contribution of the character of both individual glucan strands or chains and the higher order structure to the overall activity of the glucan product is described by Sletmoen et al. in Biopolymers vol. 89, No. 4 pp 310-321, 2008. Higher order structure may comprise a regular arrangement such as a triple helix or a more loose aggregation.

The present invention provides a glucan formulation that is perceived as a moderately sized entity when encountered by the target cells, but when phagocytosed the glucan is easily taken up into phagosomes without inducing lysosomal rupture. The present invention thus describes a novel organization of a highly potent soluble beta-glucan with good gelling properties. Without wishing to be bound by theory it seems that the glucan molecules are arranged in a type of higher complex and loose "haystack" arrangement kept together by relatively weak hydrogen bonds between the frequent —OH groups along the glucan backbone structure. The "haystack" organization has the potential of presenting a number of sites on its surface available for recognition by specific glucan receptors on the target cells. The "haystack" organized molecules do not, however, harbor the rigidity of an insoluble product, but would much more easily become "degraded" and thus "immobilized" at the site or after phagocytosis. Such a large higher order organization is advantageous as compared both to insoluble and to known soluble products since it gives an immunomodulatory response mimicking many of the effects observed with particulate and insoluble beta-glucans without inducing less controllable and possible harmful effects known to be associated with insoluble beta-glucans.

In one aspect the present invention provides a glucan having a weight average molar mass on a single chain basis of 15,000 to 50,000 g/mol and a weight average molar mass in aqueous solution on an aggregate basis of 4 to $20 \times 10^5$ g/mol, said glucan existing in gel form when dissolved in water at a concentration ≥1% at 25° C. and neutral pH and having a melting temperature (gel to sol) between 30 and 44° C., preferably about 33° C. when the glucan is dissolved in water at a concentration of 2%. The weight average molar mass values may conveniently be determined by SEC-MALS-RI analysis.

Preferably the glucan is in aqueous solution at a concentration of 1.5 to 6%, more preferably 1.5 to 5%, still more preferably 2 to 4%, most preferably about 2%. It is understood that a "gel" form can be considered an aqueous solution.

In a preferred aspect the glucan is a beta glucan, preferably it has a backbone of β(1,3) linked glucosyl residues and side chains of β(1,3) linked glucosyl residues (e.g. side chains of at least 2, 5, 10 or 20 linked glucosyl residues) attached thereto via a β(1,6) linkage.

"Neutral pH" means pH 7.

A "single chain" refers to an individual glucan molecule, i.e. one in which the glycosyl residues are covalently linked. "Aggregates" form through hydrogen bond interactions and define a supramolecular or higher order structure. Such associations are less permanent than provided by covalent bonding but the methods described herein result in recognisable patterns of aggregation, whose average molar mass can be analysed using the techniques referred to herein. The "aqueous solution" is typically pH 7.

Alternatively viewed, the present invention provides a gel glucan product comprising glucan in aqueous solution at a concentration of 1 to 6%, the glucan having a weight average molar mass on an aggregate basis of 4 to $20 \times 10^5$ g/mol and a weight average molar mass on a single chain basis of 15,000 to 50,000 g/mol, the gel glucan product having a melting temperature (gel to sol)) between 30 and 44° C., preferably about 33° C.

As mentioned, the gel glucan product has a melting temperature (gel to sol) between 30 and 44° C., preferably about 33° C. when the glucan is dissolved in water at a concentration of 2%. It will be appreciated that higher melting temperatures may be achieved by the inclusion of additional agents in the product, for instance gelling agents and/or by using a higher concentration of glucan.

Glucan products are usually particulate, semi-soluble or in some cases completely soluble in aqueous solutions, the latter either giving a fluid clear solution as described, for example, in U.S. Pat. No. 5,322,841 or some giving a viscous solution as described in Steiner et al (Prog Colloid Polymer Science 77, 1988) True gel forms of soluble beta-glucans are unusual, especially for soluble yeast glucans, but the present gel product has been found to provide excellent biological activity, in particular in wound healing, as compared to other glucan products. In wound healing it is of utmost importance to apply a pharmaceutical or medical device in a manner which secures the moisturization of the wound and the products must cover and stick to the wound surface to avoid infections and provide for an administration profile as deemed relevant by a medical practitioner or necessary due to the type of wound. Usually, glucans in their particulate, semi-soluble or liquid form do not meet these basic requirements either because they are not effective, they are in a state which is not applicable for wound healing purposes, or both. The glucan of the present invention combines these necessary characteristics thus making it useful for all applications where a pure glucan gel may find a proper use. In addition to strictly topical applications, other possible uses could be oral and/or mucosal administration, such as treating diseases of the gastro-intestinal tract or the oral cavity in addition to cancer therapy. The excellent adhesion properties of the glucan according to the present invention enable it to cover the mucosal lining at the site of action and thus accelerate the healing process. Thus the glucans of the invention have particular utility in the treatment of oral mucositis and other indications affecting the mucosa.

According to the present invention a radical heating and cooling process is performed to establish and "freeze" a preferred 3-dimensional complex and continuous glucan structure. This heating and rapid cooling establishes a gel network with a very beneficial 3-dimensional structure of the glucan chains, which shows an excellent healing profile as exemplified herein. The tertiary, or 3-dimensional, structure of a beta glucan, in this case the arrangement of the molecular chains within the glucan gel as a whole, appears to be of utmost importance for efficacy. Without establishing a limitation of being bound by theory, it seems that only biologically effective molecular structures provide for binding to different receptors at the target cells. Single chain, short chain or products not structured in an appropriate 3-dimensional complex manner will not be able to stimulate the body's immune system in the same way.

There are limited ways to characterize the 3-dimensional (also defined as tertiary or supramolecular structure) molecular structure of a gel comprised by its single chains. General ways of describing such a gel can be by the average molar mass and molar mass distribution of the single chains, as well as by physical characteristics such as viscosity. In the case of immunomodulating products, gels can also be indirectly described by their biological efficacy profile, or in other words measuring of the so-called "biological fingerprint". When using molecular mass as a defining physical characteristic, it is recognised that the analysis methods are generally destructive, leading to the analysis of the single chain components of the gel product, or smaller aggregated structures, rather than giving a detailed picture of the molecular interactions between these single chains which are necessary to give a biologically effective 3-dimensional tertiary structure. Nevertheless a detailed analysis of several other physical characteristics of glucans including their viscosity combined with a biological efficacy profile will enable the skilled man to distinguish between a variety of different glucans. One of these criteria is a specific molecular mass range. The molar mass of glucans can be determined in different ways. In the case of a soluble glucan product the molar mass is conveniently measured by SEC-MALS-RI analysis, and such analysis provides a weight average molar mass value ($M_W$) for the sample as well as the distribution of different molecular weights within the sample. In the present invention, the weight average molecular mass ($M_w$) is defined as follows:

$$M_w = \frac{\sum n_i M_i^2}{\sum n_i M_i} = \frac{\sum c_i M_i}{\sum c_i}$$

Where $n_i$ is the number of molecules with molar mass $M_i$. The weight concentration $c_i$ of molecules with molar mass $M_i$ is proportional to the molar mass $M_i$ and the number of molecules $n_i$.

$$c_i = M_i n_i => n_i = c_i / M_i$$

The weight concentration for each slice in the chromatogram is determined by the RI-detector, while the molar mass for each slice is measured by the MALS-detector in combination with the RI-detector. The calculations are based on light scattering theory.

Specifically, the average molar mass (for single chains) according to the present invention is determined by SEC-MALS-RI in DMAc with 0.5% LiCl (dimethylacetamide with 0.5% lithium chloride) assuming a dn/dc of 0.12 for the glucan in this solvent. The DMAc/LiCl solvent fully dissolves the said glucan into single chains, and subsequent SEC-MALS-RI analysis with DMAc with 0.5% LiCl as eluent therefore gives a measure of the molecular weight distribution on a single chain level. In short, the analysis of the glucan in DMAc/LiCl involves dissolution of the dry glucan in the solvent at a concentration of approximately 3 mg/ml by stirring the solution at r.t. over night and heating it at 100° C. for 1 h, prior to the analysis by SEC-MALS-RI using 3×PLgel Mixed-A LS columns and DMAc with 0.5% LiCl as eluent. The weight average molar mass for the glucan of the present invention on a single chain basis determined by this method is 15,000 to 50,000 g/mol, preferably 25,000 to 45,000 g/mol, and more preferably 30,000 to 40,000 g/mol.

In aqueous solution the weight average molar mass of the mainly higher order structures and aggregates present is 4-20×10$^5$ g/mol, preferably 5-15×10$^5$ g/mol, and more preferably 6-12×10$^5$ g/mol. These averages are calculated when very large aggregates, i.e. molar mass above 1.0×10$^7$ g/mol, are excluded. The analysis of the glucan in aqueous solution involves diluting the gel solution to approximately 3 mg/ml in 0.1 M NaNO$_3$ with 0.02% NaN$_3$, heating to 100° C. in a capped glass tube for 30 min, cooling to room temperature, filtrating through a 0.2 µm syringe filter, and analysis by SEC-MALS-RI using TSKgel G5000 PWXL+TSKgel G4000 PWXL columns and 0.1 M NaNO$_3$ with 0.02% NaN$_3$ as eluent. Similar set-ups with for example 0.05 M Na2SO4/0.01 M EDTA as solvent/eluent gives equivalent results. The combination of molar mass values for the single chains and the higher order structures/aggregates in aqueous solution gives a good indication of the molecular and tertiary structure of the gel as a whole and usefully defines the glucans of the present invention.

The glucans of the present invention are further characterized by being in gel form at 25° C. in aqueous solutions with minimum concentration of 1% and at a pH between 3 and 8. The glucan gels of the invention are further characterised by their viscosity profile exemplified by the melting temperature of the gels (gel to sol) of from 30 to 44° C., preferably above normal body temperature, more preferably between 39 and 44° C.

Figure 3:
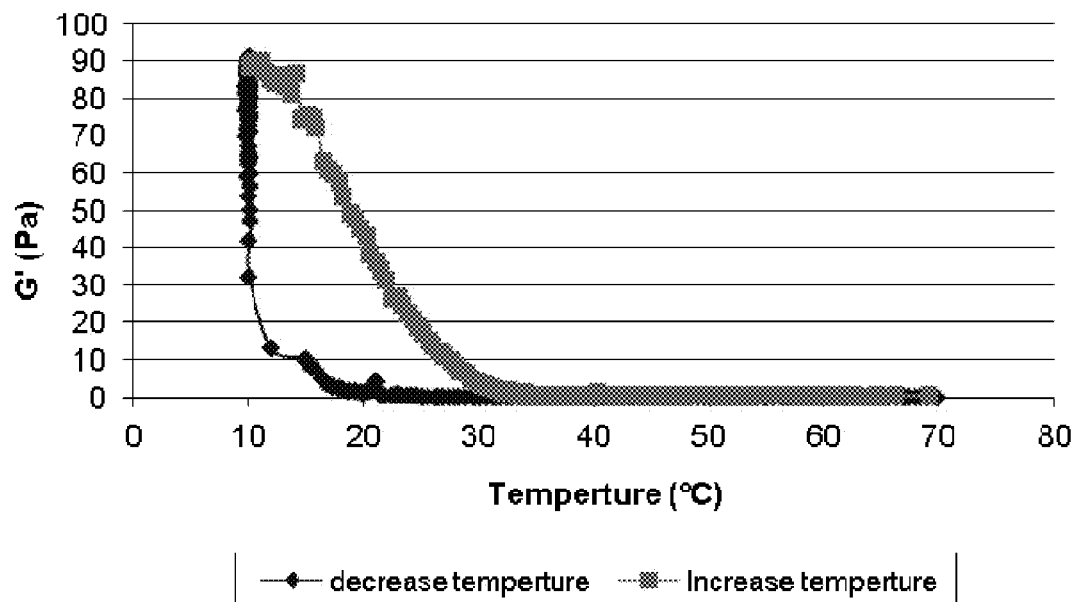

The gel melting point for a glucan product, i.e. the gel→sol transition temperature, is conveniently determined by small strain oscillatory measurements using a Stresstech HR rheometer or similar and examining the viscoelastic changes during cooling (70→10° C.) and heating (10→70° C.) of the glucan solution. An example of storage modulus (G') plotted against temperature in such an experiment is shown in FIG. 3. The melting temperature for this particular sample is equivalent to where the storage modulus of the curve for increasing temperature levels out (at approx. 0 Pa), which is approx. 33° C. Another way of determining approximate melting temperature of the gel is to measure the viscosity (e.g. using a rotational viscometer) of the gel at sequentially higher temperature until the viscosity is essentially gone and the gel has transformed into a solution. The melting temperature is preferably about 30-44° C., preferably over body temperature to guarantee a stabilized glucan gel for topical applications. Topical administration demands a comparably lower melting temperature than oral administration or administration to a site of an infection.

Figure 6:
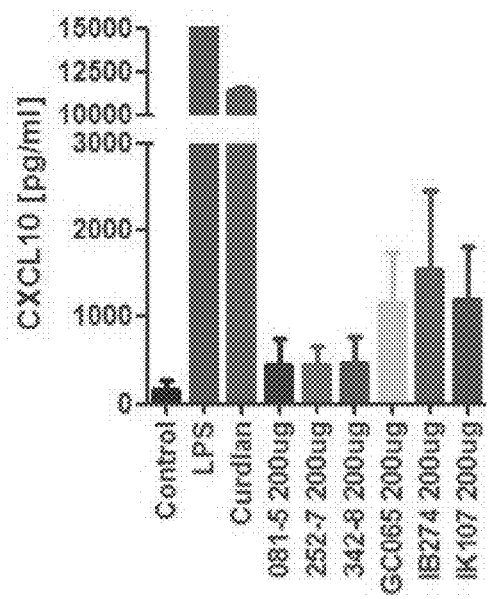

The glucan gel of the present invention is an aqueous gel and while the gel form can be confirmed by visual inspection, the non-newtonian viscosity profile and the pseudo-plastic and thixotropic nature of the glucan gel may also be determined by viscosity measurement e.g. by using a rotational viscometer. A 2% glucan gel according to the present invention has a viscosity of at least 1000 cP, preferably at least 1500 cP, measured at 25° C. and a rotational speed of 10 rpm using a Brookfield DV-II+ Pro Programmable viscometer with a small sample adapter and spindle SC4-31 (corresponding to a shear rate of 3.40 sec$^{-1}$). A convenient method for measuring the viscosity of this pseudoplastic and thixotropic gel is to use a so called up-down rate ramp, for example starting at 2 rpm and going up in 2 rpm increments to 10 rpm and then going back down again in 2 rpm steps. The data from such an experiment can both demonstrate the pseudoplastic (decreasing viscosity with increasing shear rate) and thixotropic (decreasing viscosity over time while subjected to shear) characteristics of the gel as well as provide a measure of e.g. 10 rpm viscosity. An example of such data for a 2% glucan gel is shown in FIG. 6.

The glucans of the present invention are typically derived from yeast, preferably form *Saccharomyces cerevisiae*. The basic molecular structure of these glucans is typically a β-1,3-backbone (meaning a chain of glucose molecules linked by β-1,3 linkages), in addition to β-1,3 side chains (meaning a chain of at least two glucose molecules linked by β-1,3 linkages) and a β-1,3,6-linkage point linking the side chains to the backbone. In addition, glucans from yeast comprise β-1,6 linkages which may be linked to the side chains or directly to the backbone. Further types of linkages do exist but at a comparably low level. Other yeasts which may provide a source for the glucan include Brewers yeast, *Candida* sp. like *Candida albicans, Candida cloacae, Candida tropicalis, Candida utilis, Hansenula* sp. like *Hansenula wingei, Hansenula arni, Hansenula henricii* and *Hansenula americana, Histoplasma* sp., *Kloeckera* sp., *Kluyveromyces* sp. like *Kluyveromyces lactis, Kluyveromyces fragilis, Kluyveromyces polysporus, Pichia* sp., *Rhodotorula* sp., *Saccharomyces* sp. like *Saccharomyces delbruekii, Saccharomyces rosei, Saccharomyces microellipsodes, Saccharomyces carlsbergensis* or different *Saccharomyces* strains like *Saccharomyces cerevisiae* R4 (NRRL Y-15903) and R4 Ad (ATCC No. 74181), *Schizophyllum* sp., *Schizosaccharomyces* sp. like *Schizosaccharomyces pombe, Torula* sp. and *Torulopsis* sp.

However, the gel glucans of the present invention may be derived from other suitable sources, e.g. bacterial, fungal or cereal glucans. The therapeutic activities of various glucans are well documented in the art and the processes of the present invention may be used to enhance activity of glucans in general, in particular in wound healing where the physical form and inter-molecular structure of the glucan product has been shown, by the present inventors, to be particularly significant. Without wishing to be bound by theory a rule of thumb is that the higher the weight average molar mass on a single chain basis of the glucan used according to the present invention, the more efficacious glucan gels may be produced.

The side chains of the glucan gels of the present invention usually comprise 2 or more β(1,3) linked glucosyl units. According to the present invention, single molecules linked to a main chain are not regarded as "side chains".

The glucans of the present invention preferably have side chains of, i.e. consisting or consisting essentially of, β(1,3) linked glucosyl units. In addition to the β(1,3) linked chains, the glucans may also have one or more β(1,6) linked side chains. By altering the chains of the structure it is possible to alter the characteristics of the final product. There are many different ways of altering glucans including enzyme-treatment, use of acids like formic acid or hydrochloric acid or different bases as well as by other means. Preferred glucans are those which have been treated by acid (e.g. formic acid) or enzyme or any other suitable method to significantly reduce or eliminate the number of repetitive (1,6)-linked glucose molecules within the glucan. These (1,6)-linked glucosyl moieties would normally be found in the side chains of beta-glucans derived from yeast. The resulting glucans have β(1,3) main chains and β(1,3) side chains which are linked thereto through a single β(1,6) linkage which is not cleaved off by the elimination treatment.

The preferred glucans are essentially free of repetitive β(1,6) linked glucosyl residues. The single (1,6) linkages at the branch points (the β(1,3,6)-branching points) do not provide 'repetitive' β(1,6) linked glucosyl units. By 'essentially free' is meant less than 6%, preferably less than 4% and most preferably less than 3% of the total glucosyl units.

Some treatments, such as enzyme treatments, may leave up to 4 beta-1,6-linked, but typically 2 beta 1,6 linked glucosyl units uncleaved in the side chains. Such molecules are also 'essentially free' of repetitive beta 1,6-linked glucosyl units.

The distribution of linkages within preferred glucans of the invention may be represented as follows:

| Type of linked glucosyl residue | % |
| --- | --- |
| β(1,3) | 80-98 |
| β(1,6) | 0-6 |
| β(1,3,6) | 1-8 |
| Terminal | 0.01-6 |

β(1,3,6) refers to branch point residues which are (1,3) linked in the backbone and participate in a (1,6) connection to provide a side chain.

The glucan of the present invention could be in the form of a single, extracted fraction or two or more different fractions with different average molecular weights.

The glucans are underivatized in terms of chemical modifying groups.

The glucans of the invention are generated by a novel process. The inventors have found that by performing a specific heating and cooling step a novel gel glucan product is obtained with improved activity as compared to other similar glucan products. By doing this a highly randomly organized "haystack" gel will be created without having the typical triple helical structure of "annealed" beta-glucan chains. Surprisingly it was observed that this type of gel-structure was significantly more potent as immunomodulator than a classical organized soluble beta-glucan either in triple helical conformation or multiples of helixes. According to this heating and cooling step, a solubilised beta-glucan preparation is energized in order to break up existing higher order structure and inducing a random organization with a large proportion (e.g. >40%, preferably >50%, more preferably >60% or >70%) of free single chain molecules By rapid cooling in accordance with the present invention, the molecules are "frozen" to a new molecular conformation by rapidly establishing intermolecular interactions wherein the product does not primarily form triple helical structures. The molecules are thus frozen in a more random molecular position creating a novel intermolecular organisation. This supramolecular organisation is then resulting in a final product which is in a gel form. Surprisingly these new products have a much better efficacy profile as immunomodulators compared to those not having undergone this treatment or products without such a gel structure.

Thus in a further aspect the present invention provides a method of producing a gel glucan product as defined above wherein an aqueous solution of glucan molecules is heated to a temperature of 120-130° C., preferably 120-125° C., and held at that temperature for 10-30 minutes, the glucan solution is then cooled to a temperature of 35-50° C., preferably 35-40° C., over a time period not greater than 80 minutes, preferably less than 60 minutes, e.g. 50-60 minutes.

The duration of cooling described above is based on a commercial process in which 220 litres of an aqueous solution of glucan molecules are used as the starting material. It will be appreciated that if smaller volumes are used then the duration of the cooling step may be shorter than that described above, for instance less than 50 minutes, e.g. 20 to 50 minutes.

The heating is preferably performed in an isolated and agitated tank large enough to hold the entire batch of product, with a jacket or similar structure to enable the heating of the outside of the tank. The batch size, the capacity of the heating system, the volume to surface ratio of the tank and the effect of the agitator should be balanced in such a way that the whole batch may be heated to the specified temperatures within a reasonable time period, while ensuring a homogeneous heating of the whole batch. Alternatively the energizing step may take place after the product has been filled in its final container, either by heating in an autoclave or by alternative forms of energizing, e.g. ultrasound or micro waves.

Thus in a further aspect, the present invention provides a method of producing a gel glucan product as defined above wherein an aqueous solution of glucan molecules is treated with an energy source to disturb the higher order structure between the glucan chains and then treated to allow rapid reestablishment of intermolecular interactions. As well as heating, suitable energy sources include ultrasound and micro waves. In the case of ultrasound and micro waves, it may be sufficient to allow rapid re-establishment of intermolecular interactions simply to cease exposure to the ultrasound or micro waves.

If the energizing step has been performed for the whole batch in a tank, the active cooling is preferably performed in the same tank, and will require the ability to use the jacket of the tank to cool the tank surface. Again the batch size, the capacity of the cooling system, the volume to surface ratio of the tank and the effect of the agitator should be balanced to allow cooling to take place within the specified time, while ensuring a homogeneous cooling of the whole batch. This initial cooling should be followed by the filling of product into final containers, and subsequent cooling of the containers to room temperature. Preferably the cooling step is performed immediately after the heating step, i.e. immediately (in so far as is practical with the equipment concerned) after the glucan has been held at the elevated temperature for 10-30 minutes.

A suitable procedure for performing the heating and cooling steps in an industrial process is described in Example 1.

If the energizing step has been performed in the final containers, these containers should be cooled to room temperature within the time frame described above.

The heating and cooling step described above may be repeated, e.g. once more.

The concentration of glucan in aqueous solution prior to the heating and rapid cooling step is preferably 1.5-6%, more preferably 2 to 4%, most preferably about 2%. Preferably, the concentration of glucan in the glucan gel is about 2%, for instance 1.8% to 2.2%. Therefore, preferably the concentration of glucan in aqueous solution prior to the heating and rapid cooling steps is also about 2%. The methods of the present invention do not exclude the presence of further steps in which additional agents or materials are added to the solution. If such steps are performed then the they may increase the volume of the aqueous solution and so decrease the concentration of glucan in the solution. Preferably however the volume of the solution is not changed significantly so that the concentration of glucan in the starting and end products is roughly equal. Of course, the skilled man will appreciate that, if desired, a higher concentration of glucan in the starting product can be used such that the addition of agents or materials in additional steps leads to a precise, desired glucan concentration in the final product. The skilled man will be able to calculate the appropriate glucan concentration in the starting product and the appropriate volumes of agents and materials to add to achieve a desired glucan concentration in the resulting gel product.

The above heating and cooling step may be performed on any aqueous solution of glucan molecules; preferred glucans, including glucans with modified branching, are discussed above and the glucan solution will preferably be a yeast glucan solution. The weight average molar mass ($M_w$) of the glucans in the starting solution is preferably high, preferably, on a single chain basis, the weight average molar mass of glucans in solution is above 15,000, more preferably above 20,000, most preferably above 25,000 g/mol. Suitable methods for determining these mass values are given above.

Glucans are generally extracted from their source material (e.g. fungi, yeast or cereal) in particulate form but methods of generating soluble forms from particulate glucans are known in the art and include acid or alkali treatments, such as the formolysis step described in WO 95/30022. Soluble glucan products from cereals like barley are available from Sigma Chemical. According to the present invention, a particulate starting material, such as may be prepared by the protocol in Example 1 of WO 95/30022, will preferably be solubilised by heating in formic acid for at least two hours. Formolysis performed on particulate glucan starting material may conveniently cause selective removal of any β(1,6) linked glucosyl side chains as well as solubilising the particulate glucan.

The methods of the invention also preferably comprise a preliminary heating step, prior to the above described heating and rapid cooling step, where the formic acid treated product is boiled (>100° C.) for at least 30 mins. After the product has cooled it is preferably treated to remove particulate materials by regular methods know in the art e.g. by centrifugation or filtration.

The particulate glucan which is treated to yield a soluble form for processing in accordance with the present invention is preferably derived from cell walls, in particular yeast cell walls, which have had the protein components and other remnants like mannan and chitin removed therefrom e.g by washing.

One example of a suitable particulate yeast glucan product is produced by Biotec Pharmacon ASA which is derived from Bakers Yeast (*Saccharomyces cerevisiae*) and known as NBG Cos®. Another example of particulate glucan raw materials are whole glucan particles like the product Imprime WGP™. NBG Cos® is a natural underivatized (in terms of chemical modifying groups) particulate β(1,3)/(1,6) glucan, characterised by NMR and chemical analysis to consist of polymers of beta-1,3-linked D-glucose containing side-chains of beta-1,3 and beta-1,6-linked D-glucose.

The visual appearance of preferred gel products of the present invention is firm, opaque and whitish with a high adhesion capacity to other surfaces.

In a further aspect the present invention provides a glucan product obtained or obtainable by any of the aforementioned processes.

The glucans of the present invention are potent therapeutic agents and in a further aspect the present invention provides the glucans as described herein for use in therapy, in particular for the treatment of conditions where a subject is in need of a systemic or local enhancement of the immune response, e.g. where there is tissue damage or infection. The glucans are of particular utility in assisting wound or ulcer healing and in the treatment of oral mucositis and cancer or reducing tumour size.

In a further aspect the present invention provides therefore a method of assisting wound or ulcer healing or treating oral mucositis in a subject in need thereof which comprises administration to said subject of a glucan of the present invention as described herein.

Reference is made to "assisting" wound or ulcer healing because some wounds or ulcers will heal naturally and others may not but the glucans of the invention have been shown to accelerate wound and ulcer healing. In some cases, healing may not occur satisfactorily without treatment. An example for such a wound which demands treatment for healing is diabetic foot ulcer. In this indication the patient develops wounds based on the underlying cause which is diabetes. Due to the often untreated underlying cause and the fact that these wounds are to be found on the feet of patients, these ulcers do not heal by themselves and cause huge problems for the patient usually ending in amputation of the foot.

In a further aspect the present invention provides a method of treating cancer or reducing the size of a tumour in a subject which comprises administration to said subject of a glucan of the present invention as described herein. Preferably the glucan is administered orally. Preferably, the glucan is administered at a dosage of 5 to 200 mg/kg/day, more preferably 20 to 100 mg/kg/day.

In a further aspect the present invention also provides a pharmaceutical composition comprising a glucan in gel form as defined above and one or more pharmaceutically acceptable diluents or carriers, preferably water and optionally one or more physiologically acceptable stabilisers or further diluents or carriers. The compositions may conveniently be formulated into any topical dosage form. The topical dosage forms may be creams, lotions, solutions, gels, ointments, pastes, sprays, films, etc.

In some variations, the compositions as described herein are in the form of an ointment. The ointment base may be an oleaginous base, an emulsifiable base, an emulsion base, or a water-soluble base. In other variations, the compositions according to the present invention are in the form of a cream. The creams may be viscous liquids or semisolid emulsions, either oil-in-water or water-in-oil. The cream bases may be water-washable, and contain an oil phase, an emulsifier, and an aqueous phase. In yet further variations, the compositions of the present invention are in the form of a lotion. The lotions may be formulated as suspensions of solids and contain suspending agents to produce better dispersions. The compositions according to the present invention may also be formulated pastes. Pastes are semisolid dosage forms in which the active agent is suspended in a suitable base. Depending on the nature of the base, pastes are divided between fatty pastes or those made from a single-phase aqueous gels.

In some variations, the compositions form a film on the wound surface. To aid film formation, film forming agents such as, but not limited to, acrylic acid and its derivatives, polyacrylic and its derivatives such as polybutylmethacrylate and polymethacrylic acid, polymethacrylate, ascorbyl palmitate, carbomer, carnauba wax, cellulose derivatives such as cellulose acetate phthalates, rosca mellose sodium, hydroxyethyl cellulose, hydroxypropyl cellulose, hydroxypropyl methylcellulose, ethyl cellulose and related compounds, hydroxypropyl methylcellulose phthalate, hypromellose phthalate, cetyl alcohol and derivatives, microcystalline wax, poloxamer, polyethylene glycol, polyurethane, polyvinyl acetate, polyvinyl acetate phthalate, polyvinyl alcohol, silicone rubber and derivatives, shellac, triglycerides derivatives, and combinations thereof are used.

The compositions can also include at least one film plasticizer agent that may serve to soften the polymer film formed by the film forming agent so that it is sufficiently flexible to move with area of the body applied without cracking or peeling.

In some variations, the compositions may be cast into a film prior to application to the wound or applied to the wound directly where they polymerize in situ. A "spread-on" film polymerizes when applied to the skin and may be delivered as a cream or ointment from a tube, roll-on, spray, and the like. The film may be created by incorporating a silicone rubber, into the external phase. Upon mixing with the internal phase, the resultant emulsion is allowed to cure and provides a "spread-on" film, which polymerizes when applied to the wound. The emulsion may be spread onto a substrate to achieve a desired thickness.

In other instances, the compositions may be preformed into a layer or patch. The patch may be of varying thickness. The patch may also be cut to have a shape that generally follows the wound edges.

In some variations, the patches may include a pharmaceutically acceptable adhesive material that serves to affix the patch to the wound or skin. A patch backing layer may also be included.

When used as a spray, the compositions according to the present invention may include at least one organic solvent.

The compositions may be directly placed on a wound, or placed on a substrate for application on a wound. Any substrate (carrier) may be used with compositions described here. For example, woven, non-woven, knitted, foam, and adhesive substrates may be used. Absorbent or non-absorbent substrates may also be used. In some variations, the compositions are sprinkled or spread on the substrate. In other variations, the compositions are impregnated within the substrate.

The wound dressings may be applied for any suitable time period. For example, they may be applied over a time period of one day, over several days, over several weeks, or for several months or more. In general, the wound dressings will be reapplied until the wound is healed. The duration of wound treatment with the dressings described here may depend on such factors as the type of wound being treated, wound location, and form of the composition being applied. Depending on the form used, the composition may be removed with water, or wiped or peeled off the wound.

The compositions described here may be used to treat wounds resulting from any etiology. For example, the wounds may be due to burns, infections, ischemia, lymphedema, neoplasms, neuropathy, radiation damage, surgical procedures, venous insufficiency, and trauma. The compositions of the present invention are of particular utility in assisting wound or ulcer healing.

The invention further provides a physical support, for example any medical device or material for medical use having applied thereto, including impregnated therein, a glucan of the invention as defined herein.

One important characteristic of such beta glucans is their water holding capacity and gel formation characteristics even in the absence of conditions like non-neutral pH or cations which might promote gel healing. Some beta-glucans would form gels at concentrations as low as 1%, but more typically in the range of 2-4%. A soluble beta-glucan from yeast like the one described herein will form a thixotropic and pseudoplastic gel when dissolved in aqueous solution at a concentration of 1-6% in pH range from 3-7, independent of the presence of cations.

The compositions of the invention preferably comprise 1.5-6% beta glucan in an aqueous solution, more preferably the composition comprises around 2-5% glucan in an aqueous solution. The use of different concentrations is dependent on the purpose and the different modes of administration. As a general rule, a yeast glucan as described above with a concentration of more than 4-5% in an aqueous solution and free from other stabilizing substances would result in a final gel product which is difficult to manufacture due to its solid gel properties.

Encompassed by the terms 'wound' and 'ulcer' are surface wounds, surgical wounds, burns, open fractures, leg ulcers, apthous ulcers, diabetic ulcers and decubitus ulcers. Wounds may be as a result of injury, surgery or disease but all are characterised by a loss of dermal integrity, the skin may be torn, cut or punctured and regrowth of the skin is required to seal the opening. The glucans of the present invention have been shown to accelerate wound closure. As shown in the Examples, efficacy can readily be demonstrated by measuring the size of an open wound.

The compositions are preferably applied topically, e.g. as a gel, transdermal patch, lotion, ointment, cream etc. Compositions may be applied daily, more frequently or less frequently, e.g. twice daily or on alternate days and for a duration as determined by a clinician or in some cases by the patient or other health advisor. The duration of treatment will depend on the nature and severity of the wound or ulcer with progress generally being readily determined by visual inspection.

Topical administration includes administration in the mouth and suitable, gels, lozenges, pastes, sprays etc. for delivery to the oral mucosa are known in the art.

The glucans and compositions containing them find utility in human and veterinary medicine. As used herein, the term 'medical' includes veterinary applications and contexts. Humans are preferred subjects for treatment but other animals which may usefully be treated include livestock and companion animals.

The glucans of the invention and compositions containing them may be applied to or incorporated in a physical/solid support such as a patch, dressing, plaster, bandage, film, gauze etc. which can be applied to the wound or ulcer site and such products constitute a further aspect of the present invention.

The glucans of the present invention also find corresponding utility in in vitro applications for the culturing of skin cell lines, e.g. for use in skin grafts. Thus in a further aspect the present invention provides an in vitro method of proliferation of skin cells which comprises contacting a population of skin cells with glucans of the invention as described herein.

It will be appreciated that preferred features applicable to one aspect or embodiment of the invention apply, mutatis mutandis, to all aspects and embodiments.

The glucans of the present invention have excellent in vivo efficacy as anti-cancer agents and wound healing agents, as shown in the Examples. The Examples also show the ability of the glucans of the invention to stimulate production of cytokines which are relevant in a variety of therapeutic contexts. The Examples show that the preferred glucans of the present invention trigger the expression of TNFα and CXCL2/MIP2α in mouse peritoneal macrophages. A weak induction, compared to the curdlan or LPS responses, of TNFα is also seen in human myeloid dendritic cells derived from peripheral blood monocytes.

The effect of the preferred beta glucans on release of TNFα is dose-dependent and appears to diminish at glucan concentrations above a certain threshold value eg. 2-4 μg/ml in a variant of the RAW cell line overexpressing the beta glucan receptor dectin-1. A moderate to low induction of TNFα and CXCL-2 is special to the products of the present invention. Both TNFα and CXCL-2 are instrumental in wound healing. The murine chemokine CXCL2 stimulates cell migration and angiogenesis, and can be used as surrogate marker for angiogenic activity in the inflammatory granulation tissue.

The preferred glucans of the present invention do not trigger a powerful expression of IP-10 (CXCL-10). IP-10 is a member of the alpha or cysteine-X amino acid-cysteine (CXC) chemokine family of chemotactic cytokines. High levels of IP-10 expression have been detected in a number of chronic human inflammatory conditions, including psoriasis, a common inflammatory disease of the skin. Patients have generally shown an abnormal wound healing response characterized by a more intense inflammatory phase and a prolonged and disorganized granulation phase with impaired blood vessel formation. The glucans of the present invention should not enhance the LPS-induced expression of IP10 from human dendritic cells, and preferably inhibit the LPS induced expression of IP-10 from macrophages harvested from db/db mice. This shows that the preferred glucans according to this invention turn on beneficial elements of the wound healing process while they turn off inhibitors leading to a prolonged healing phase.

In addition, the Examples show the ability of the gel glucans of the invention to activate the complement system as demonstrated by accumulation of terminal complement complex (TCC).

The invention will now be further described in the following non-limiting Examples and the figures in which:

FIG. 1 illustrates the SEC-MALS-RI chromatograms of a number of batches of branched β(1,3) glucan with <2% repetitive β(1,6) linked glucosyl units analyzed in DMAc with 0.5% LiCl assuming a dn/dc=0.12. As can be seen the molecular weight distribution is in the range of approx. 10,000 g/mol to approx. 200,000 g/mol on the single chain level.

Figure 2:
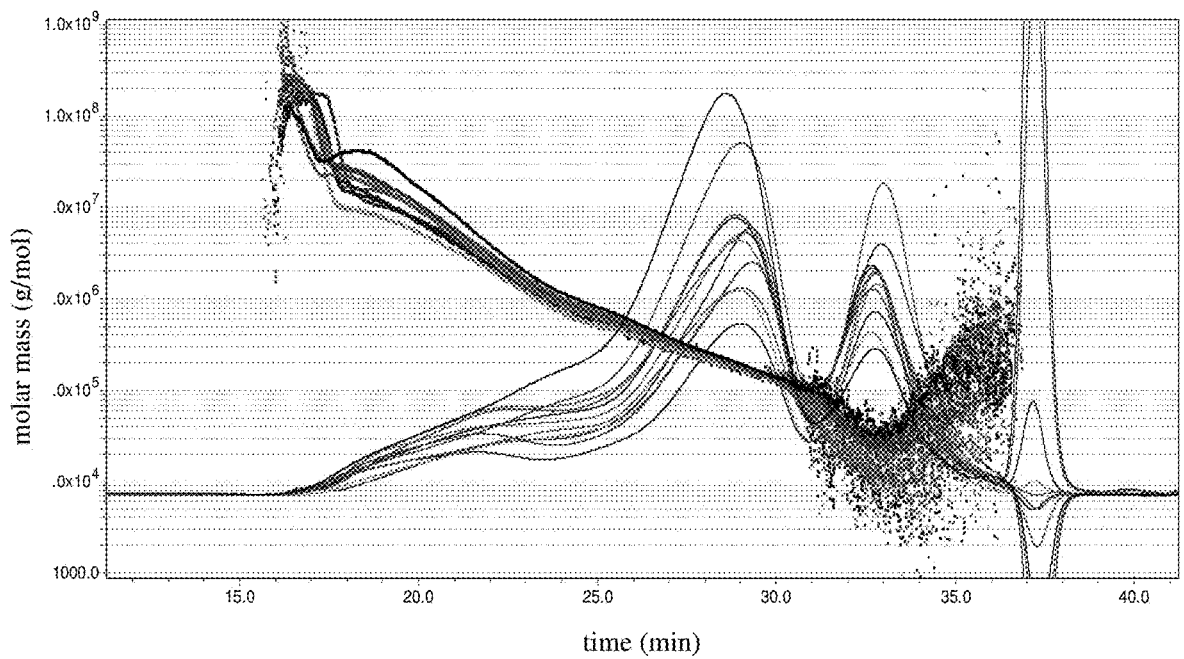

FIG. 2 shows SEC-MALS-RI chromatograms of a number of batches of the glucan product analyzed in aqueous buffer (0.1 M $NaNO_3$) assuming a dn/dc=0.15. As can be seen the molecular weight distribution is in the range of approx. 10,000 g/mol to above 10,000,000 g/mol. The aqueous SEC-MALS-RI results, in combination with the results in DMAc/LiCl, show that the glucan exist as aggregates in the aqueous solution.

FIG. 3 shows storage modulus, G' (Pa), plotted against temperature for a glucan gel according to the present invention. The data was obtained by small strain oscillatory measurements using a Stresstech HR rheometer and the following temperature scan: 70 to 10° C. at a rate of ⅓° C./min, kept at 10° C. for 2 h and then 10 to 70° C. at a rate of ⅓° C./min. The melting temperature of this gel (gel to sol) is determined to approximately 33° C. based on where the increasing temperature curve levels out (G'≈0 Pa).

Figure 4:
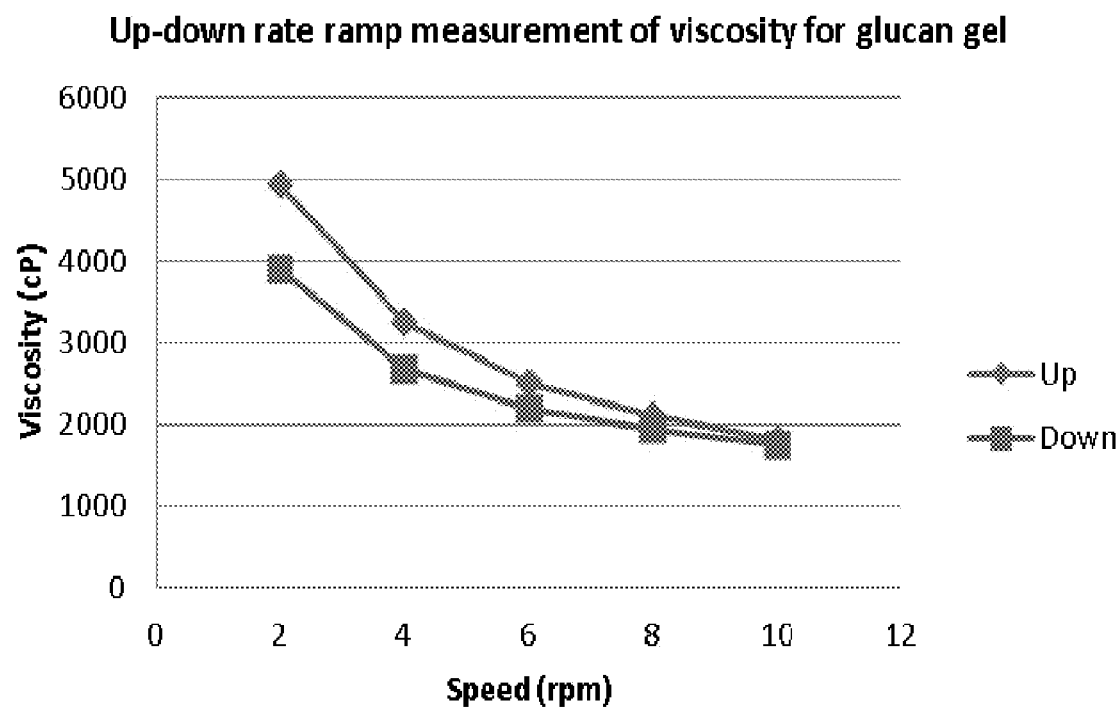

FIG. 4 shows the viscosity measurements of a 2% glucan gel according to the present invention using an up-down rate ramp method. The data was obtained at 30° C. with an equilibration time of 3 min at 2 rpm prior to first measurement and 30 sec equilibration before measurement on each consecutive speed after that. Calculated 10 rpm viscosity was 1772 cP from the IPC Paste model in the Rheocalc software of Brookfield Engineering Inc.

Figure 5:
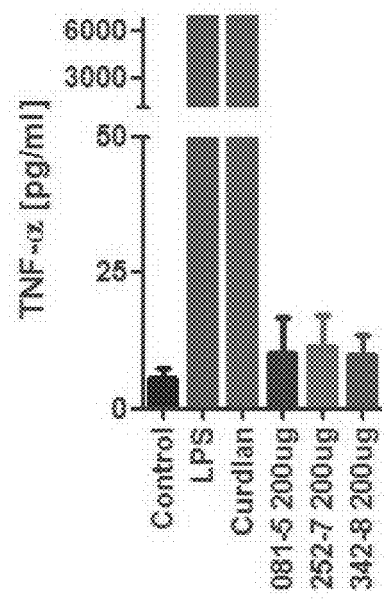

FIG. 5 describes the release of TNF-α from human myeloid dendritic cells derived from peripheral blood monocytes cultured in the presence of 200 µg/ml of the glucan gel of the present invention, curdulan or LPS. The cytokine was measured in culture medium supernatants at 24 h post-stimulation using a commercially available ELISA kit.

FIG. 6 illustrates the release of CXCL10 (IP10) from human myeloid dendritic cells derived from peripheral blood monocytes cultured in the presence of 200 µg/ml of the glucan gel of the present invention, curdlan or LPS. The chemokine was measured in culture medium supernatants at 24 h post-stimulation using a commercially available ELISA kit.

Figure 7:
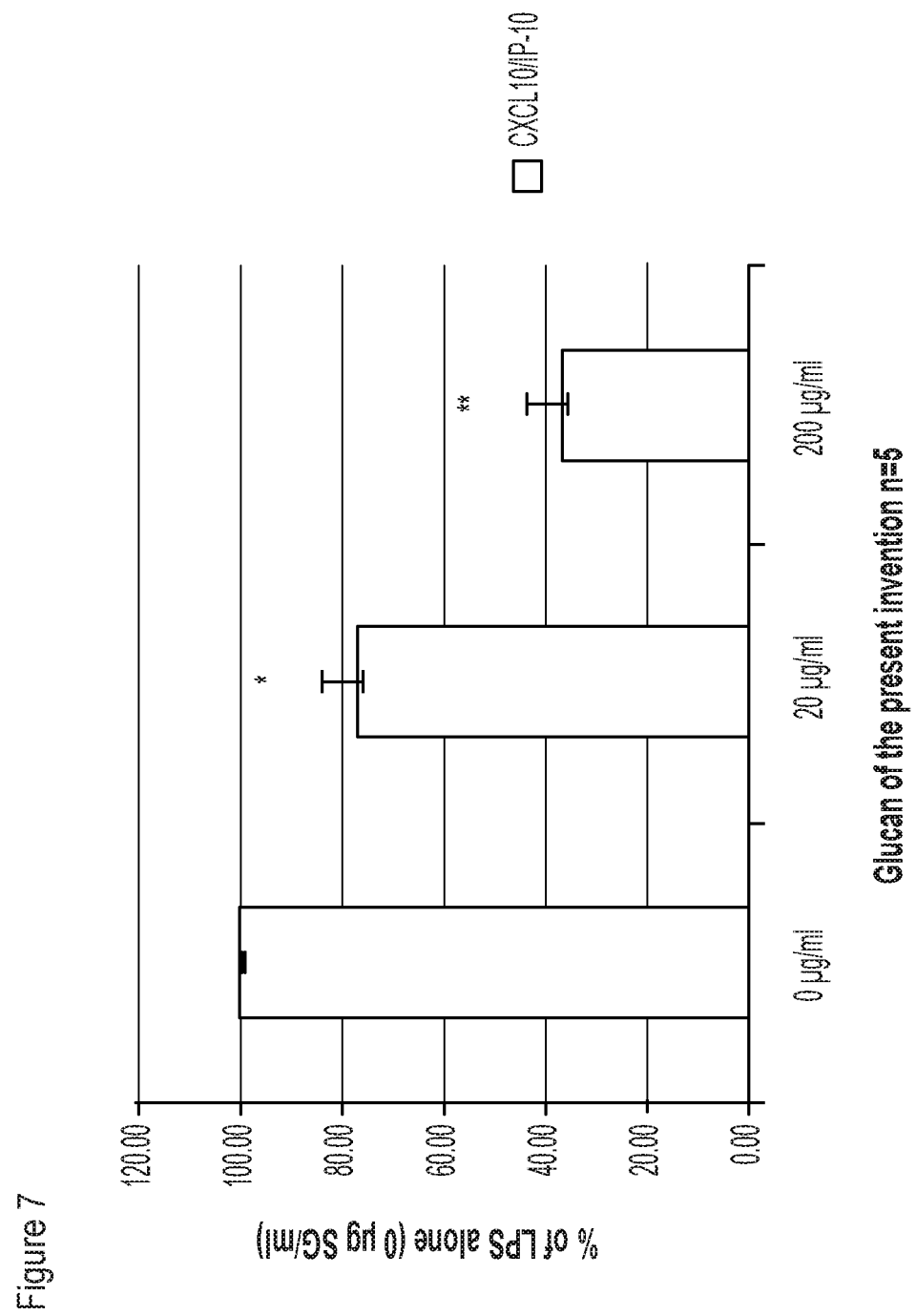

FIG. 7 shows the secretion of CXCL-10 from macrophages harvested from db/db mice costimulated in vitro by LPS and the glucan gel of the present invention. Lane 1; LPS alone, lane 2; LPS+20 µg/ml of the glucan gel of the present invention, lane 3; LPS+2 µg/ml of the glucan gel of the present invention. *$p<0.05$. *$p<0.01$.

Figure 8:
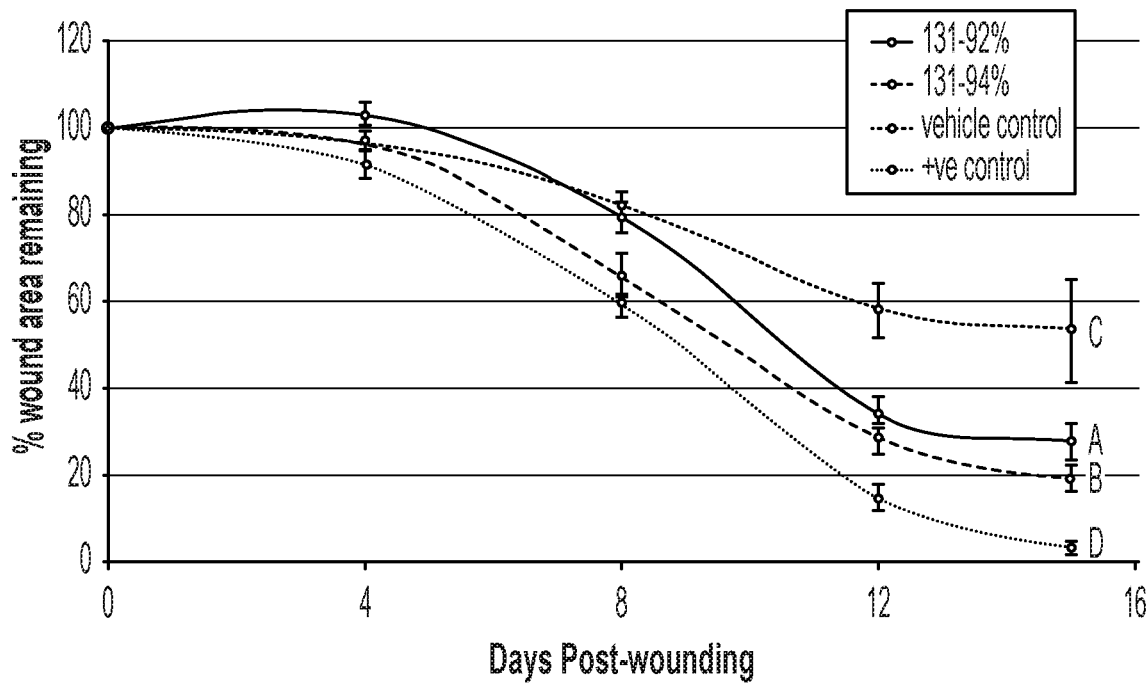

FIG. 8 shows the results of a wound healing trial using the glucan gel according to the present invention in a 2% and 4% concentration in an aqueous solution compared to a growth factor cocktail with a known efficacy profile. The dressing+water was used as vehicle control. Both 2% and 4% concentrations are effective, with 4% being more effective, although less effective than the GF cocktail.

Figure 9:
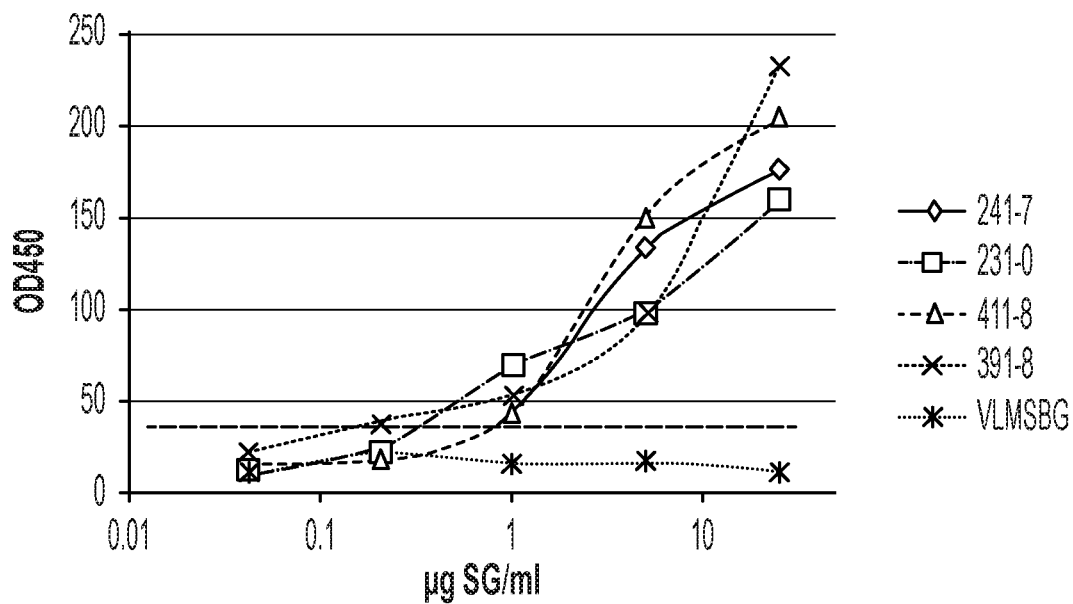

FIG. 9 shows activation of complement by different batches of beta-glucans. Accumulation of fluid-phase terminal complement complex in human serum was measured. 241-7, 231-0, 411-8, 391-8 are beta-glucans in gel form representing glucans of the present invention. VLMSG represent a non-complement activating formulation of a soluble beta-glucan which is not in gel form. The horizontal dotted line represents the spontaneous complement activation in human serum.

Figure 10:
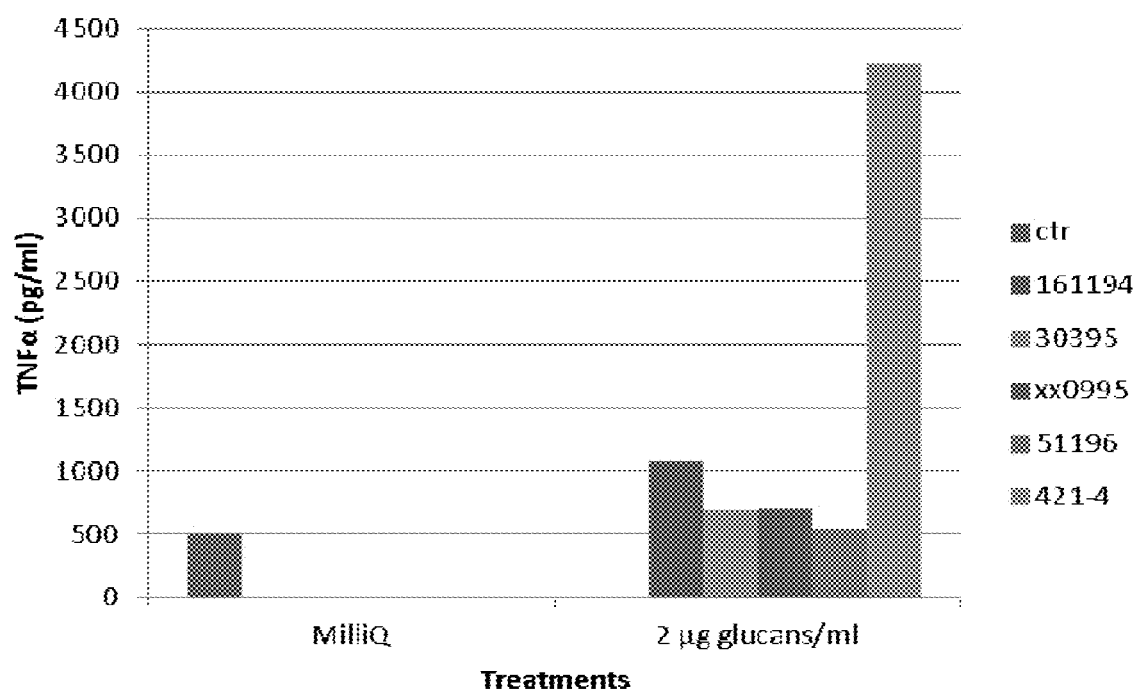

FIG. 10 shows secretion of TNFα from a dectin-1 over-expressing RAW cell-line variant. The soluble yeast beta glucan 421-4 represents a glucan of the present invention, while 161194, 30395, xx0995 and 51196 are clear, non-gelling variants.

Figure 11:
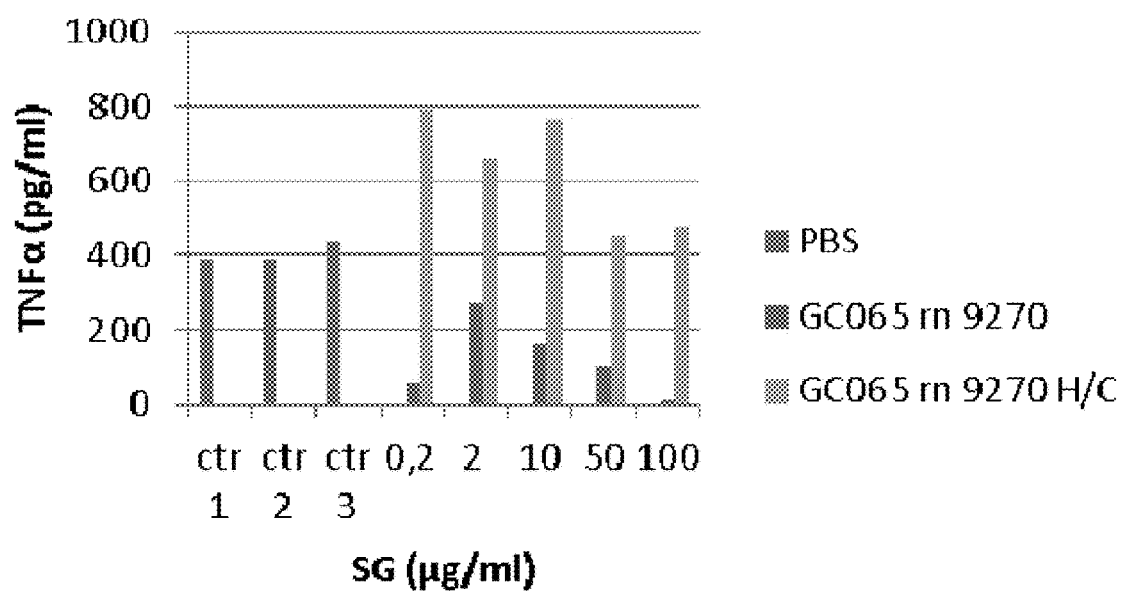

FIG. 11 shows the biological effect in the dectin-1 over-expressing RAW cell line of soluble glucan (SG) subjected to heating and rapid cooling (HC) as described in Example 1. GC065 rn 9270 is a soluble glucan product with a broken gel, as described in Table 1. Treatment according to Example 1 rescues the biological effect of the broken product.

Figure 12:
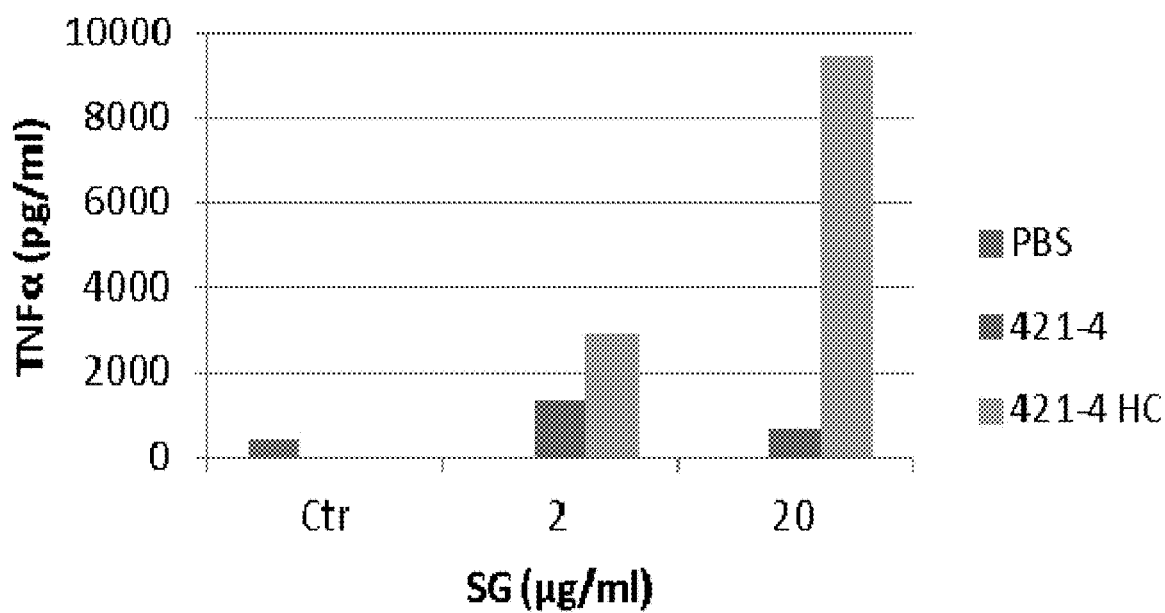

FIG. 12 shows the biological effect in the dectin-1 over-expressing RAW cell line of soluble glucan (SG) subjected to heating and rapid cooling (HC) as described in Example 1. 421-4 is a SG product corresponding to the product described as a soft gel in Table 1. Treatment according to Example 1 enhances the biological effect of SG batch 421-4.

EXAMPLES

Example 1

Preparation of Gel Glucan Product of the Present Invention

An aqueous solution of 1.5 to 2% yeast glucan molecules was treated as described below. This aqueous solution was prepared from a particulate glucan preparation by formolysis to selectively remove β-1,6 side chains and subsequent purification and diafiltration to remove particulate matter and low molecular weight components from the formolysis solution. A suitable formolysis step is disclosed in Example 3 of EP 0759089 B1. The particulate glucan was itself prepared from cell walls of Baker's Yeast (S. cerevisiae) by separate extractions with alkali, ethanol and water, each extraction being followed by appropriate drying (spray drying and vacuum drying).

a. Heat Treatment:

Heat treatment takes place after the concentration of the glucan solution has been adjusted, normally giving a product volume of approximately 220 liters at a temperature of approximately 60° C., in a closed and agitated 800 liter tank which is heated by introduction of steam to a jacket surrounding the tank.

The product is heated slowly to approximately 105° C. to ensure an even heating of the whole batch, and then more quickly to 123° C. Normal heating time from 60 to 123° C. is 40-50 minutes. The product is then held at 123-125° C. for 20 minutes.

b. Active Cooling:

Active cooling is then started. It is operated manually, by direct opening and closing of hand operated valves. First the steam is carefully evacuated from the jacket to drain, and the drain valves are left open. Cooling water is then carefully introduced to the jacket, slowly at first to avoid excessive thermal stress to the steel of the tank. As the temperature drops the flow of water is increased. Cooling is normally continued until the product temperature reaches 35-40° C. Normal cooling time from 123 to 40° C. is 50-60 minutes.

Example 2

In Vivo Wound Healing in Mouse Model

The impact of test glucans and controls on wound healing was investigated by analysing the repair of full-thickness excisional skin wounds in the diabetic (db/db) mouse model (i.e. BKS.Cg-m Dock7$^m$+/+Lepr$^{db}$/J mice). Upon acclimation (5-7 days without disturbance) the animals were housed in groups of 5 animals according to Home Office regulations and the specific requirements of diabetic animals. After experimental wounding, animals were housed in individual cages (cage dimensions 35×15×15 cm with sawdust bedding, changed twice weekly), in an environment maintained at an ambient temperature of 23° C. with 12-hour light/dark cycles. The mice were provided with food (Standard Rodent Diet) and water ad libitum. Following all anaesthetic events, animals were placed in a warm environment and monitored until they were fully recovered from the procedure. All animals received appropriate analgesia (buprenorphine) after surgery and additional analgesics as required. All animal procedures were carried out in a Home Office licensed establishment under Home Office Licences (PCD: 50/2505; PPL: 40/3300; PIL: 50/3482; PIL: 70/4934). The health of animals was ill monitored on a daily basis throughout the study.

On day 0, animals were anaesthetised (isofluorane & air) and the dorsum shaved and cleaned with saline-soaked gauze. A single standardised full-thickness wound (10.0 mm×10.0 mm) was created in the left dorsal flank skin of each experimental animal. Wounds in all treatment groups were subsequently dressed with a circumferential band of the transparent film dressing Bioclusive™ (Systagenix Wound Management, UK); after which they received a glucan or control by injection 50 µl of a 2% solution in purified water through the Bioclusive film using a 29-gauge needle. Diabetic animals were randomized to one of the treatment regimes using appropriate software. For the experimental groups receiving glucan treatments was reapplied on post-wounding days 2, 4 and 6. Wound sites in these animals were closely monitored for excessive build-up of applied agents and excessive wound site hydration; if excessive applied agent accumulation/hydration was apparent, previously applied material was removed by aspiration prior to reapplication. For the positive control group treatments was reapplied daily until post-wounding day 6—wounds in this group received a total of 7 applications of the growth factor combination treatment. On post-wounding days 4, 8 and 12 all animals were re-anaesthetised, their film dressings and any free debris removed, and their wounds cleaned using saline-soaked sterile gauze. After photography on days 4 and 8, wounds were re-dressed as above with Bioclusive film dressing. Healing was determined as wound closure relative to the wound size at day 0.

The results are shown in Table 1 and FIG. 8 below.

TABLE 1

Treatment of wounds in diabetic mice

| Product | Healing wounds, Day 8 | Healing wounds, day 12 | Healing wounds, day 15 |
|---|---|---|---|
| Negative control (dressing only) | 0/10 | 1/10 | 2/10 |
| Vehicle control (water + dressing) | 1/10 | 3/10 | 4/10 |
| Broken gel product | 3/10 | 7/10 | 7/10 |
| Soft gel glucan (2%) | 5/10 | 9/10 | 10/10 |
| Solid gel glucan (4%) | 8/10 | 10/10 | 10/10 |
| Positive control (GFcoctail) | 10/10 | 10/10 | 10/10 |

The soft gel glucan product and the solid gel glucan product are both yeast derived glucans which have been prepared by the methods of the present invention. Both are yeast derived glucans which have been treated with formic acid to remove β(1,6) linked glucosyl units found in the native yeast glucan side chains. The solid and soft gel glucans have been prepared using the new heating and rapid cooling protocol described herein (Example 1). Surprisingly the solid gel (a 4% product) demonstrates enhanced wound healing activity as compared to the soft gel glucan product (a 2% product).

The "broken gel product" describes a yeast derived glucan product where the (inter-molecular) conformation of the molecules in the gel has been destroyed to a large degree by exposure to an agent which interferes with hydrogen bonding. This glucan is not able to exert a similar beneficial efficacy/healing profile compared to the gel product of the invention. This result clearly shows that the gel structure of the glucan according to the present invention is a surprisingly important property for in vivo efficacy.

The results clearly show that the use of a glucan gel produced according to the invention elicits a more potent response in wound treatment models compared to the delivery vehicle and negative control. The fact that the "broken gel" product gives inferior results also points to the necessity of the existence of an intact gel structure or specific high order conformation within a glucan gel.

Example 3

Determination of Molar Mass

The molar mass of a series of yeast glucan products was determined using size exclusion chromatography as previously defined in the description. The experiment was performed with the glucan in aqueous solution and thus gives molar mass values for the glucan aggregates within the glucan sample and not on a single chain bases. 5 glucan samples were tested, all were derived from yeast and all had their β(1,6) linked side chains diminished. 4 were in solution and the 5th was a gel glucan in accordance with the present invention (prepared in accordance with Example 1).

The calculated average molar mass for the four glucans in aqueous solution varied from $1.0\text{-}3.74 \times 10^5$ g/mol.

The glucan of the invention had an average molar mass of $8 \times 10^5$ g/mol.

In other experiments, the glucans of the present invention had molar masses which varied from $5\text{-}15 \times 10^5$ g/mol.

Example 4

Determination of Melting Point

Determination of the melting point of a glucan gel produced according to the present invention was performed as described in the description and the results are shown in FIG. 3.

Example 5

Viscosity Measurements

Determination of the viscosity of a glucan gel produced according to the present invention (prepared according to Example 1) was performed as described in the description and the results are shown in FIG. 4.

Example 6

Biological Activity

The effect of the gel glucans of the present invention, which were prepared as different batches, each according to Example 1, on the release of TNFα and CXCL-2 and -10 is described herein and shown in the Figures.

In addition, the ability of the beta glucans to activate the complement system was measured. The complement system is composed of a series of serum proteins. The system is a part of the innate immune system, and is activated upon infection or detection of pathogen associated molecular patterns. Activation of the system results in a cascade of cleavage of the complement proteins, which ultimately leads to formation of a terminal complement complex (TCC). Accumulation of TCC can be measured by detection of a neo-epitope using monoclonal antibodies, and can thus serve as an indicator of complement activation.

The glucan was diluted (1:10) in human serum to a volume of 100 The mixture was incubated at 37° C. for 30 min, then diluted 1:5 in PBS before the relative amount of fluid-phase TCC was determined in triplicate using a commercially available ELISA-test kit for human TCC. The results are shown in FIG. 9.

The soluble beta-glucan of the present invention, in gel form, activates the complement system in human serum. However, activation of complement is not a common feature of soluble beta-glucans, as exemplified by VLMSG in FIG. 9. The molecular weight of VLMSG range from $10^3$ to approximately $5 \times 10^6$ g/mol, with a mean value $1,3 \times 10^4$ g/mol, and yields a clear solution.

It was demonstrated that gel-forming soluble yeast beta glucans of the present invention prepared according to Example 1 stimulate the release of TNFα from dectin-1 over-expressing RAW cells, while non-gelling, clear, variants of soluble yeast beta glucans apparently do so to a much lesser extent (FIG. 10).

The invention claimed is:

1. A gel glucan product obtainable by
   a) heating an aqueous solution of soluble yeast glucan molecules to a temperature of 120° C. to 130° C. and holding the solution at that temperature for 10 to 30 mins; and
   b) cooling the glucan solution to a temperature of 35° C. to 50° C., over a time period of less than 80 minutes,
   wherein said glucan is present in said gel glucan product at a concentration of 1 to 6%, has a weight average molar mass of 15,000 to 50,000 g/mol on a single chain basis and a weight average molar mass in aqueous solution on an aggregate basis of 4 to $20 \times 10^5$ g/mol, and wherein said gel glucan product has a gel to sol melting temperature between 30° C. and 44° C.

2. The gel glucan product of claim 1, wherein said glucan has a weight average molar mass of 20,000 to 40,000 g/mol on a single chain basis.

3. The gel glucan product of claim 1, wherein said glucan has a weight average molar mass of 25,000 to 30,000 g/mol on a single chain basis.

4. The gel glucan product of claim 1, wherein said glucan is in aqueous solution at a concentration of about 2%.

5. The gel glucan product of claim 1, wherein said glucan is derived from *Saccharomyces cerevisiae*.

6. The gel glucan product of claim 1, wherein said glucan is a beta glucan comprising a backbone of β-(1,3)-linked glucosyl residues and side chains comprising 2 or more β-(1,3)-linked glucosyl residues, the sidechains being attached to the backbone via a β-(1,6)-linkage.

7. The gel glucan product of claim 1, wherein said glucan is essentially free of repetitive β(1,6) linked glucosyl residues.

8. The gel glucan product of claim 1, wherein said gel glucan product has a gel to sol melting temperature of about 33° C.

9. The gel glucan product of claim 1, wherein in step a) the glucan is held at the temperature of 120° C. to 130° C. for about 20 minutes.

10. The gel glucan product of claim 1, wherein in step a) the aqueous solution of glucan molecules is heated to a temperature of 120° C. to 125° C.

11. The gel glucan product of claim 10, wherein in step a) the glucan is held at the temperature of 120° C. to 125° C. for about 20 minutes.

12. The gel glucan product of claim 1, wherein the glucan is cooled over a time period of 50 to 60 minutes.

13. The gel glucan product of claim 1, wherein said method is preceded by a formolysis step wherein a particulate glucan starting material is suspended in formic acid in order to remove β-(1,6) linked glucosyl side chains and to solubilise the particulate glucan.

14. The gel glucan product of claim 13, wherein the formolysed product is filtered through a mesh of about 0.2 μ.

15. The gel glucan product of claim 1, which is present in a pharmaceutical composition also comprising one or more pharmaceutically acceptable diluents or carriers.

16. A physical support having applied thereto or impregnated therein the gel glucan product of claim 1.

17. The physical support of claim 16, wherein said physical support is selected from the group consisting of a woven, non-woven, knitted, foam or adhesive substrate; a patch, dressing, plaster, bandage, film or gauze.

* * * * *